(12) United States Patent
Højlund Nielsen et al.

(10) Patent No.: US 10,722,871 B2
(45) Date of Patent: Jul. 28, 2020

(54) SULFIDE-BASED ALKANE DEHYDROGENATION CATALYSTS

(71) Applicant: HALDOR TOPSØE A/S, Kgs. Lyngby (DK)

(72) Inventors: Poul Erik Højlund Nielsen, Fredensborg (DK); Rasmus Munksgård Nielsen, Humlebæk (DK); Lived J. Lemus-Yegres, Copenhagen S (DK)

(73) Assignee: HALDOR TOPSØE A/S, Kgs. Lyngby (DK)

( * ) Notice: Subject to any disclaimer, the term of this patent is extended or adjusted under 35 U.S.C. 154(b) by 0 days.

(21) Appl. No.: 16/079,304

(22) PCT Filed: Mar. 7, 2017

(86) PCT No.: PCT/EP2017/055275
§ 371 (c)(1),
(2) Date: Aug. 23, 2018

(87) PCT Pub. No.: WO2017/162427
PCT Pub. Date: Sep. 28, 2017

(65) Prior Publication Data
US 2019/0054453 A1    Feb. 21, 2019

(30) Foreign Application Priority Data
Mar. 22, 2016   (DK) ................. 2016 00174

(51) Int. Cl.
| | | |
|---|---|---|
| *B01J 27/051* | (2006.01) |
| *B01J 27/043* | (2006.01) |
| *B01J 27/047* | (2006.01) |
| *B01J 27/30* | (2006.01) |
| *C07C 5/32* | (2006.01) |
| *B01J 37/20* | (2006.01) |
| *B01J 37/18* | (2006.01) |
| *B01J 37/02* | (2006.01) |
| *B01J 27/04* | (2006.01) |
| *B01J 38/18* | (2006.01) |
| *B01J 38/64* | (2006.01) |
| *B01J 35/00* | (2006.01) |
| *B01J 35/10* | (2006.01) |

(52) U.S. Cl.
CPC ........... *B01J 27/0515* (2013.01); *B01J 27/04* (2013.01); *B01J 27/043* (2013.01); *B01J 27/047* (2013.01); *B01J 27/051* (2013.01); *B01J 27/30* (2013.01); *B01J 37/0201* (2013.01); *B01J 37/18* (2013.01); *B01J 37/20* (2013.01); *B01J 38/18* (2013.01); *B01J 38/64* (2013.01); *C07C 5/321* (2013.01); *C07C 5/322* (2013.01); *B01J 35/006* (2013.01); *B01J 35/1042* (2013.01); *C07C 2523/75* (2013.01); *C07C 2527/04* (2013.01); *C07C 2527/043* (2013.01); *C07C 2527/047* (2013.01); *C07C 2527/049* (2013.01); *C07C 2527/051* (2013.01); *Y02P 20/52* (2015.11); *Y02P 20/584* (2015.11)

(58) Field of Classification Search
CPC ........ B01J 27/0515; B01J 37/20; B01J 37/18; B01J 37/0201; B01J 27/04; B01J 27/051; B01J 38/18; B01J 38/64; B01J 27/043; B01J 27/047; B01J 27/30; B01J 35/006; B01J 35/1042; B01J 38/12; C07C 5/321; C07C 5/322; C07C 2523/75; C07C 2527/04; C07C 2527/043; C07C 2527/047; C07C 2527/049; C07C 2527/051; Y02P 20/584; Y02P 20/52
See application file for complete search history.

(56) References Cited

U.S. PATENT DOCUMENTS

| | | |
|---|---|---|
| 3,275,705 A | 9/1966 | Box |
| 3,280,210 A | 10/1966 | Johnson et al. |
| 3,296,325 A * | 1/1967 | Alexander ............... C08F 20/54 585/260 |
| 3,387,054 A | 6/1968 | Schuman |
| 3,530,060 A | 9/1970 | Offenhauer |
| 3,560,060 A | 2/1971 | Morris |
| 3,718,607 A | 2/1973 | Martin |
| 4,589,722 A | 5/1986 | Hall et al. |

(Continued)

FOREIGN PATENT DOCUMENTS

| | | |
|---|---|---|
| CA | 448474 A | 5/1948 |
| CN | 103861619 A | 6/2014 |
| CN | 104069778 A | 10/2014 |

(Continued)

OTHER PUBLICATIONS

Danish Search Report dated Oct. 17, 2016, for Danish priority application No. PA 2016 00174 (9 pages).

(Continued)

*Primary Examiner* — Ali Z Fadhel
(74) *Attorney, Agent, or Firm* — Buchanan Ingersoll & Rooney P.C.

(57) ABSTRACT

A catalyst for the dehydrogenation of alkanes to alkenes comprises a catalytically active material supported on a carrier, wherein the catalytically active material is a metallic sulfide (MeS) comprising Fe, Co, Ni, Cu, Mo or W or any combination of two or more metals selected from Pb, Sn, Zn, Fe, Co, Ni, Cu, Mo and W. The catalyst is regenerated in several steps. The dehydrogenation is carried out at a temperature between 450 and 650° C. and a pressure from 0.9 bar below ambient pressure to 5 bar above ambient pressure.

12 Claims, No Drawings

(56) References Cited

U.S. PATENT DOCUMENTS

2004/0092784 A1 5/2004 Legendre

FOREIGN PATENT DOCUMENTS

| | | | | |
|---|---|---|---|---|
| CN | 104069779 A | 10/2014 | | |
| CN | 104607168 A | 5/2015 | | |
| EP | 0568303 A2 * | 11/1993 | ............ | B01J 8/0453 |
| EP | 0568303 A2 | 11/1993 | | |
| GB | 984901 A | 3/1965 | | |
| WO | 0170655 A1 | 9/2001 | | |

OTHER PUBLICATIONS

International Search Report (PCT/ISA/210) dated Jun. 21, 2017, by the European Patent Office as the International Searching Authority for International Application No. PCT/EP2017/055275.

Written Opinion (PCT/ISA/237) dated Jun. 21, 2017, by the European Patent Office as the International Searching Authority for International Application No. PCT/EP2017/055275.

* cited by examiner

SULFIDE-BASED ALKANE DEHYDROGENATION CATALYSTS

The present invention relates to the use of sulfide-based catalysts in processes for the dehydrogenation of alkanes to the corresponding alkenes.

Basically, the catalytic dehydrogenation of lower alkanes is a simple, but yet important reaction, which can be illustrated by the dehydrogenation of propane to propene in accordance with the reaction:

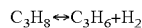

$$C_3H_8 \leftrightarrow C_3H_6 + H_2$$

With the ever growing demand for light olefins, i.e. lower aliphatic open-chain hydrocarbons having a carbon-carbon double bond, catalytic dehydrogenation is growing in importance. Especially the dehydrogenation of propane and isobutane are important reactions used commercially for the production of propylene and isobutylene, respectively. Propylene is an important basic chemical building block for plastics and resins, and the worldwide demand for propylene has been growing steadily for decades. It is expected that the demand growth for propylene will soon be equal to or even higher than that for ethylene. One of the major applications of isobutylene is as feedstock in the manufacture of methyl-tert-butyl ether (MTBE).

The process shown above is endothermic and requires about 125 kJ/mole in heat of reaction. Thus, in order to achieve a reasonable degree of conversion the dehydrogenation process is taking place at a temperature around 600° C. The dehydrogenation of isobutene is similar to that of propene in every respect, apart from requiring a slightly lower temperature.

There are 3-4 commercial processes for alkane dehydrogenation in existence, using 3 different catalysts. The differences between these processes deal with the supply of the heat of reaction. The processes and the catalysts will be briefly described below.

a) The Catofin (Houdry) Process

This process is characterized by the heat of reaction being supplied by pre-heating of the catalyst. The Catofin process is carried out in 3-8 fixed bed adiabatic reactors, using a chromium oxide/alumina catalyst containing around 20 wt % chromium oxide. The catalyst may be supplemented with an inert material having a high heat capacity, or alternatively with a material which will selectively combust or react with the hydrogen formed, the so-called heat generating material (HGM). Promoters such as potassium may be added.

The Catofin process is a very well-established process and still the dominant industrial dehydrogenation process. Since the reaction heat is supplied by the catalyst, a sequential operation is used, during which the catalyst bed is used for dehydrogenation. Then the gas is purged away, and the catalyst is being regenerated/heated and the Cr(VI) oxide reduced with hydrogen. Finally, the bed is purged with steam before another dehydrogenation.

b) The Snamprogetti-Yarzintez Process

This process is a fluid-bed version of the above process, using twin fluidized beds, one each on process and regeneration duty with catalyst cycling between them. Numerous plants are in operation, e.g. in the former Soviet Union and in Saudi Arabia.

The catalyst deactivation may be due to mechanical reasons, stress induced during heating-cooling cycles and solid state reactions, such as diffusion of chromium into the alumina lattice. This is, however, secondary to the desire to get rid of chromium, which is the real challenge in this process because the toxicity of chromium is a problem. More specifically, the presence of chromium in the catalyst makes it an environmental and health hazard to handle. This is particularly so because chromium(VI)oxide, $CrO_3$, and related compounds of chromium in oxidation state VI are easily formed by oxidation of the catalyst. Thus, every kind of handling of the catalyst during manufacture, transport, loading and unloading is a potential hazard, and with the increasing demand for dehydrogenation processes it is desirable to find effective, less toxic dehydrogenation catalysts.

c) The Oleflex Process

The Oleflex process employs noble metal catalysts, especially a promoted $Pt/Al_2O_3$ catalyst in a reaction system of 3-4 moving bed reactors with the catalyst being continuously regenerated in a separate regeneration circuit. The heat of reaction is supplied by pre-heating the hydrocarbon stream. The noble metal catalyst is subject to slow deactivation. Thus, in the Oleflex process the catalyst moves down in the radial flow bed. In the bottom, the catalyst is transported to a regeneration reactor, where the carbon on the catalyst is burned away and the platinum is redispersed by means of a chlorine treatment. The regenerated catalyst is recycled back into the top of the dehydrogenation reactor. The cycle time is up to one week.

The noble metal is supported on an alumina carrier, and it is stabilized by means of tin and possibly other promoters. Platinum is a good catalyst choice from a technical point of view and it forms stable alloys with tin. The main problem with this kind of catalyst is the high price, which is currently counteracted by aiming to decrease the platinum loading.

d) The STAR Process

The STAR® process (STAR being an acronym for STeam Assisted Reforming) is a commercially established dehydrogenation technology, which has some attractive features.

Steam is being used as a diluent, and the process takes place in a tubular reactor like a steam reformer placed in a furnace. The reaction heat is supplied by firing with natural gas. The catalyst is Pt supported on a $ZnAl_2O_4$ spinel. Zn and Pt form some very stable alloys. Some carbon deposition takes place, and the catalyst has to be regenerated every eight hours. The process is sometimes seen with a second reactor, in which a selective hydrogen combustion takes place along with further dehydrogenation. Presumably a noble metal catalyst is also being used here.

Like in the Oleflex process above, the challenge here is the noble metal cost. It would therefore be desirable to replace the noble metal with a base metal, i.e. a common and inexpensive metal.

It has now been found that dehydrogenation of alkanes is possible using a new generation of metal sulfide catalysts, which are easy to manufacture and remain in their active phase during operation. These metal sulfides are sulfides of metals selected from Fe, Co, Ni, Cu, Mo and W or any combinations of two or more metals selected from Pb, Sn, Zn, Fe, Co, Ni, Cu, Mo and W.

Thus, the present invention relates to a catalyst for the dehydrogenation of alkanes to alkenes, said catalyst comprising a catalytically active material supported on a carrier, wherein the catalytically active material comprises a metallic sulfide (MeS), which is a semiconductor, and wherein the catalyst is regenerated in several steps.

The regeneration involves the following reactions:
(a) conversion of the sulfide into sulfate, and
(b) conversion of carbon into carbon oxides.

Both reactions are highly exothermic oxidation reactions. In order to avoid any temperature runaway, they are preferably carried out using dilute air.

Thus, the steps for regeneration comprise oxidation in dilute air for the conversion of the sulfide into the corresponding sulfate and conversion back to the sulfide by reduction in dilute hydrogen containing some hydrogen sulfide. Preferably, the oxidation is carried out at a temperature between 350 and 750° C., most preferably at a temperature between 400 and 600° C.

Further, the invention relates to a process for the dehydrogenation of alkanes to the corresponding unsaturated alkenes and hydrogen ($H_2$) comprising contacting the alkane with a catalyst supported on a carrier, said catalyst comprising a metallic sulfide (MeS) supported on a carrier and comprising Fe, Co, Ni, Cu, Mo or W or any combination of two or more metals selected from Pb, Sn, Zn, Fe, Co, Ni, Cu, Mo and W. The dehydrogenation is carried out at a temperature between 450 and 650° C., preferably at a temperature between 520 and 620° C.

The dehydrogenation is carried out at a pressure from 0.9 bar below ambient pressure to 5 bar above ambient pressure, preferably at ambient pressure or at a pressure from 0.5 bar below ambient pressure up to ambient pressure.

In the process, the feed gas contains sulfur in an amount determined such that
(a) the equilibrium reaction $MeS+H_2 \leftrightarrow Me+H_2S$ is shifted towards MeS throughout the reactor, and
(b) the sulfur content is sufficient to avoid carbide formation throughout the reactor.

The reason for assigning a specific semiconductor feature to the metallic sulfide is that applicant's intensive examination of catalysts based on sulfides of metals selected from Fe, Co, Ni, Cu, Mo and W and combinations of two or more metals selected from Pb, Sn, Zn, Fe, Co, Ni, Cu, Mo and W has revealed that the activity and selectivity of these catalysts are a function of both the sulfur phase as determined by the gas composition, primarily the $H_2/H_2S$ ratio, and the temperature. In this connection it was found that the catalysts, or more specifically the metal sulfides, are semiconductors.

As pointed out above, two classes of catalysts have so far found significant industrial application: The one used in the Oleflex process is platinum-based and thus quite expensive. The other one, which is used in the Catofin process, is based on chromium oxide, which is toxic and therefore undesirable from a health and environmental point of view. The sulfide catalysts of the invention can be applied in both the Oleflex and the Catofin processes as well as in new process designs.

Dehydrogenation catalysts are widely described in the art. Thus, U.S. Pat. No. 3,560,060 A describes a dehydrogenation catalyst comprising mixtures of nickel sulfide and tungsten sulfide, cobalt sulfide and molybdenum sulfide or nickel sulfide and molybdenum sulfide supported on adsorbent carriers such as alumina, silica-alumina and silica-zirconia. Also a process for dehydrogenating isobutene to isobutene at temperatures of 370 to 565° C. and subatmospheric pressures is disclosed. U.S. Pat. No. 3,718,607 A describes a dehydrogenation catalyst comprising nickel sulfide or cobalt sulfide or combinations thereof supported on activated alumina. Further, a process for dehydrogenating alkanes to alkenes at 550 to 625° C. with addition of sulfur to the feed stream is disclosed.

EP 0 568 303 A2 discloses a catalyst for dehydrogenation of organic compounds, such as alkanes to alkenes, which comprises a sulfided combination of nickel and lead on a base-treated non-acidic support. Sulfur is added to the feed stream in order to maintain catalyst selectivity, but it is not disclosed that this addition shifts the equilibrium towards the metallic sulfide.

In U.S. Pat. No. 3,387,054 A, an alkane dehydrogenation catalyst, e.g. comprising nickel sulfide and molybdenum sulfide supported on activated alumina containing 5% silica, is described. A process for the dehydrogenation of alkanes to alkenes with $H_2S$ as by-product using a metal sulfide catalyst is also disclosed.

Also WO 01/70655 A1 describes a dehydrogenation catalyst comprising supported metallic sulfides, such as sulfides of W, Ni, Mo, Cu and Co or mixtures thereof. A dehydrogenation process for converting alkanes to alkenes with $H_2S$ as a by-product at temperatures of 300 to 650° C. and pressures of 0.05 to 50 bar is also disclosed.

As such, the use of metal sulfide catalysts for the dehydrogenation of alkanes is known in the art. For instance, processes for preparing alkenes from alkanes using metal sulfide catalysts are described in GB 488.651 A (1938) and in U.S. Pat. No. 3,280,210 A (1966). More recently, an article by Guowei Wang, Chunyi Li and Honghong Shan (ACS Catal. 4(4), 1139-1143, 2014) describes the use of metal sulfide catalysts supported on silica, in which the metal is Zn, Cu, Mn, Mo, Fe, Co or Ni, for isobutane dehydrogenation to isobutene. The catalysts are said to be highly efficient in the activation of C—H bonds for isobutane dehydrogenation, and the dehydrogenation performance is said to be better than that of the two commercial catalysts $Cr_2O_3/Al_2O_3$ and $Pt—Sn/Al_2O_3$. However, the metal sulfides described in the Guowei et al. article present a very low stability, as shown in FIG. 2 of the article, since an initially high catalytic activity drops very dramatically after the first point of measurement, i.e. after about an hour. Thus it may be doubtful whether any catalytic activity is taking place at all, even though the authors claim that this is the case.

A number of pending Chinese patent applications deal with dehydrogenation of alkanes and catalysts for that purpose. Thus, CN 104607168 A describes catalysts and a preparation method for catalytic dehydrogenation of alkanes, where the catalysts comprise components A and B wherein component A is selected from oxides of Fe, Zn, Cu, Co or Ce and component B is selected from $SiO_2$, $Al_2O_3$, $ZrO_2$, $Ga_2O_3$ and MgO. These catalysts are said to have a high degree of conversion and a high olefin selectivity, thereby making them useful in a circulating fluidized bed reactor.

CN 104069778 A discloses a fluidized bed reactor and a method for dehydrogenation of alkanes with the aid of a catalyst comprising an active ingredient of Fe, Co, Ni, Cu, Zn, Mo, W or Mn element in one or several mixed oxides or composite oxides, where the carrier is $SiO_2$, $Al_2O_3$, $ZrO_2$, $CeO_2$, CaO, $P_2O_5$, MgO or $Nb_2O_5$. A very similar reactor and method is described in CN 104069779 A.

CN 104607168 A describes a catalyst for catalytic dehydrogenation of alkanes and a preparation method thereof, where the catalysts comprise components A and B, in which component A is selected from oxides of one or more elements of La, Fe, Zn, Cu, Co or Ce, and component B is selected from mixed oxide or composite oxide formed from one or more materials of $SiO_2$, $Al_2O_3$, $ZrO_2$, $Ga_2O_3$ and MgO.

CN 103861619 A discloses sulfide catalysts for dehydrogenation of alkanes, comprising an active component and a carrier, wherein the active component is one or more elements selected from Fe, Co, Ni, Cu, Zn, Mo, W and Mn. The content of active component in the catalyst (calculated as the oxide having the highest valence) is 0.5-40 wt %, the carrier is a mixed oxide or composite oxide formed from one or more materials selected from $SiO_2$, $Al_2O_3$, $ZrO_2$, $La_2O_3$, $CeO_2$, CaO, $P_2O_5$, $Nb_2O_5$ and MgO, and the carrier content is 60-99.5 wt %. The active component on the surface of the alkane dehydrogenation sulfide catalyst exists in sulfide form.

The applicant has found that the results claimed in the above CN documents are unrealistic and not scientifically founded.

In dehydrogenation processes, such as the Oleflex process, it is normal practice to add substantial amounts of sulfur to the process in order to protect the material. Thus, in a substantially standard plant, an amount of dimethyl disulfide corresponding to a concentration of $H_2S$ in the gas phase of 70 ppm will be used.

The properties of sulfide catalysts used according to the present invention are summarized in Table 1 below.

TABLE 1

Sulfide catalyst properties

| Sulfide catalyst | Melting point, ° C. | Kp($H_2/H_2S$) at 600° C. | Band gap at room temp, eV |
|---|---|---|---|
| CoS | 1195 | 371 | 0.9 |
| $Co_3S_4$ | Decomp. at 655° C. | 32 | 1.15 |
| $Cu_2S$ | 1130 | 2900 | 1.2-1.5 |
| FeS | 1194 | 3000 | ~0, metal-like |
| $Fe_7S_8$ | 1208 | 450 | n.d. |
| NiS | 1000 | 57 | 0.4 |
| $Ni_3S_2$ | 800 | 700 | n.d. |
| ZnS | 1185 | $\sim 10^8$ | 3.5/3.9 (Wu/Sph) |
| MnS | 1610 | $2.4 \cdot 10^{10}$ | 3.2 |
| SnS | 882 | 630 | 1.3 |
| $MoS_2$ | 1185 | 21000 | 1.3-1.4 |
| $WS_2$ | 1250 | 6000 | 1.1 |
| $Ga_2S_3$/GaS | 1090/965 | 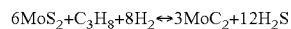 $10^6/10^8$ | 3.4/2.5 |

At equilibrium, most of the metal sulfides will remain as sulfides, in particular if the sulfur concentration is above 100 ppm. Furthermore, they are in particular close to a phase boundary non-stoichiometric compound, and the defect concentration depends strongly on the $H_2S/H_2$ ratio. Reference is made to the phase diagrams and thermodynamic data given in "Landolt Bornstein Numerical Data and Functional Relationship in Science and Technology *New Series*, eds. O. Madelung and W. Martienssen. Group IV: Macroscopic Properties of Matter". Thermodynamic considerations are based upon the HSC Chemistry for Windows, Outokompi, Finland (2002).

Some of the sulfides will have a homogeneity range, notably Co, Cu, Ni and Fe. Defects could relate to active sites and metal-like behavior to hydrogen transfer.

TABLE 2

$H_2S$ partial pressure at sulfide-carbide interface at 600° C.

| Phases | $P_{H2}$ 0.03, $P_{C3H8}$ 0.3 | $P_{H2}$ 1.0, $P_{C3H8}$ 1.0 |
|---|---|---|
| $MoC/MoS_2$ | $3 \cdot 10^{-3}$ | $1.2 \cdot 10^{-2}$ |
| $Mo_2C/MoS_2$ | $1.7 \cdot 10^{-4}$ | $1.9 \cdot 10^{-3}$ |
| $WC/WS_2$ | $1.7 \cdot 10^{-2}$ | $6.5 \cdot 10^{-2}$ |
| $W_2C/WS_2$ | $1.7 \cdot 10^{-4}$ | $2.0 \cdot 10^{-2}$ |
| $Ni_3C/NiS$ | $1.8 \cdot 10^{-3}$ | $1.4 \cdot 10^{-2}$ |
| $Fe_3C/FeS$ | $3.4 \cdot 10^{-4}$ | $2.6 \cdot 10^{-3}$ |
| $Fe_3C/CuFeS_2$ | $1.3 \cdot 10^{-3}$ | $1.6 \cdot 10^{-2}$ |
| $Fe_3C/Cu_5FeS_4$ | $1.8 \cdot 10^{-3}$ | $2.3 \cdot 10^{-3}$ |
| $Fe_3C$/stabilized FeS (in ZnS or $Cu_2S$) | $1.4 \cdot 10^{-5}$ | $1.1 \cdot 10^{-4}$ |

Some data in the above Table 1 are taken from Pearce et al., Rev. Mineral Geochem. 61, 127-180 (2006). It is noted that some of the iron sulfides are metal-like. The band gap energy of the semiconductor will decrease at increasing temperature as discussed by O'Donnell and Chen, Appl. Phys. Lett. 58, 2924-2926 (1991), and increase for small particles as calculated by Kane, Cohen and Silbey, Chem. Mater. 8, 1919-1924 (1996), for small particles of PbS. Shape dependency of the band gap energy for $MoS_2$ and $WS_2$ should also be pronounced, in particular for monolayers where values close to zero have been reported (Splendiani et al., Nano Lett. 10, 1271-1275 (2010), Mak et al., Phys. Rev. Lett. 105, 136805 (2010) and Zhao et al., ACS Nano 7(1), 791-797 (2013)).

Mo, W and Fe may form carbides, typically at $H_2S$ levels around 1000 ppm at 600° C., see Table 2 above. At lower temperatures, less sulfur is required; note the reactions $$6MoS_2+C_3H_8+8H_2 \leftrightarrow 3MoC_2+12H_2S$$

$$9FeS+C_3H_8+5H_2 \leftrightarrow 3Fe_3C+9H_2S$$

MoC is only existing at very high temperatures. This may probably also be the case for WC. Iron forms mixed sulfides with a number of elements. The ternary compounds with Cu are well-known, cf. Table 2 above. In $CuFeS_2$ (chalcopyrite) and $Cu_5FeS_4$ (bornite), it is in oxidation state 3 (~$Fe_2S_3$), but a stable compound ($CuFe_2S_3$, cubanite) is known, in which iron is in oxidation state 2. No thermodynamic data are available. In the last row in Table 2 a stabilization corresponding to the one in bornite has been assumed.

Column 2 of the above Table 2 corresponds to a Catofin case, whereas column 3 is largely representative of an Oleflex case.

The traditional hydrotreating catalysts are based upon Co/Ni-Mo/W sulfides, and the active phases are viewed as $MoS_2$ containing some Co, resulting in sulfur defects at the crystallite edges. In other words, there is a synergistic effect between Co and Mo.

Sulfur and hydrocarbon reactions constitute an area which has been subject to much research. Sulfur is known as being a poison for a number of catalysts, but it is also well-known that many reactions can be controlled by careful addition of sulfur. The steam reforming of methane is just one example, in which small amounts of sulfur suppress the formation of carbon (J. R. Rostrup-Nielsen, J. Cat. 85, 31-43 (1984)). In industrial practice, sulfur is often added in order to protect process equipment, for example in steam cracking of hydrocarbons or in the Oleflex dehydrogenation process. U.S. Pat. No. 5,489,722 to Resasco et al. describes a process in which partially substituted nickel surfaces are used for dehydrogenation, and it may well be possible that sulfur is also controlling the selectivity of the platinum-catalyzed dehydrogenation process.

The versatility of sulfide catalysts is large. In addition to the dehydrogenation reactions discussed above, sulfide catalysts are also known to catalyze a number of different hydrocarbon synthesis reactions, such as methanol and higher alcohols synthesis reactions. The reactions typically take place in the 300° C. region at an elevated pressure, and the active phase may be a carbide. The water-gas shift (WGS) reaction is also catalyzed by sulfide catalysts and takes place at a far more rapid rate than the hydrocarbon synthesis reactions. Commercial catalysts for the WGS reaction have been available for decades.

The invention is illustrated further in the examples which follow. The first examples (1-14) illustrate the preparation of sulfide catalysts according to the invention, and examples 15-20 describe the subsequent testing of some of these catalysts.

The catalyst testings have been carried out in a tubular reactor specifically built for high temperature application, such as tar reforming, and as such it is suitable for testings requiring gases containing sulfides. The reactor has a length of around 100 cm and an internal diameter of 10 mm. The catalysts to be tested are placed on a grid connected to a thermocouple which measures the inlet temperatures. Isothermal control is ensured by four independent heating zones. The tests are carried out using a 10% propane in nitrogen mixture, to which hydrogen, nitrogen and $H_2S$ can be added. The typical $H_2S$ concentration can vary from 50 ppm up to 0.5%, although the low values are associated with some uncertainty due to wall effects. This means that the $H_2S/H_2$ ratio can be varied from $10^{-3}$ to $10^{-1}$. An eventual carbide formation requires a separate consideration as done later for Fe and Mo.

The typical test conditions have been a temperature between 560 and 600° C. using 5 g of the catalyst to be tested in 2-5 mm fractions. Some of the test gases are listed in Table 3 below. Ideally, the pressure should be low, but due to pressure drop incidents in the system the typical pressure has been between 0.2 and 0.3 MPa.

TABLE 3

Test gas compositions

| Gas no | Flow | $C_3H_8$ % | $H_2$ % | $H_2S$ % | $N_2$ % | $H_2/H_2S$ i | $H_2/H_2S$ o |
|---|---|---|---|---|---|---|---|
| 1 | 55 | 9.1 | 8.7 | 0.36 | bal. | 24 | 29 |
| 2 | 51 | 9.8 | 1.8 | 0.20 | bal. | 9 | 19 |
| 3 | 25.5 | 9.8 | 1.8 | 0.20 | bal. | 9 | 19 |
| 4 | 25.5 | 9.8 | — | 0.004 | bal. | 0 | 500 |
| 5 | 55 | 9.1 | 8.2 | 0.9 | bal. | 9 | 11 |
| 6 | 55 | 9.1 | 5.5 | 0.008 | bal. | 0 | 500 |
| 7 | 51 | 9.8 | — | 0.004 | bal. | 0 | 1000 |

In Table 3, flow is Nl/h; bal. is balance; I=inlet; o=outlet

The test cycle will typically conclude with Gas 1 at 600° C., and the evaluation of the activities will be based on their performance at this condition.

The effluent gases are measured by gas chromatography.

Blind tests conducted both with an empty reactor and with 5 g of catalyst support gave the same surprising result that the $CH_4$, $C_2H_4$ formation was almost solely due to the empty reactor and also that some dehydrogenation took place, most likely at the reactor wall. For the typical test conditions 560-600° C., the amount of propene corresponded, on carbon basis, to the amount of $C_1$ and $C_2$. Calculations of the dissociation due to the empty space in the reactor are in good agreement with the experimental results. It is noteworthy that these homogeneous reactions taking place at elevated temperatures most likely are the cause for the reduced selectivity of the industrial reactions, in particular the Oleflex process, in which the gas is pre-heated to above 600° C. four times before entering the dehydrogenation reactor. The catalytic reaction is highly selective; in fact, when the results are corrected for the empty reactor contribution, a selectivity close to 100% is achieved. Ethane formation was pronounced in the presence of catalysts. However, compared to the amount that should have been present if the equilibrium amount was formed, the hydrogenation of ethylene was far from complete, indicating that ethylene is a primary product from the homogeneous propane dissociation.

The first tests were done using a reactor with a thermowell made in the same material. The testings showed a severe sulfide corrosion. Thus, a change was made to another reactor and thermowell. This reactor had an internal diameter of 15 mm versus the 10 mm diameter in the former. This made the amount of $C_1$ and $C_2$ increase by 50%.

The result reported has been corrected by assuming a selectivity of 50% in the empty reactor. Thus, on carbon basis the carbon in $C_1$ and $C_2$ equals the propylene formed by the empty reactor. The rate for the catalyst has been corrected for this contribution.

The catalysts tested in the examples 14-18 are sulfides of Cu, Fe, Ni, Co and Mo, respectively. In Example 19, the traditional Co—Mo catalyst is tested.

EXAMPLE 1

13.9 g $Cu(NO_3)_2.2.5H_2O$ is dissolved in 37.5 g water. The solution is used to impregnate 50 g of support (pv=1 ml/g).

The sample is rolled for 1 hour, dried overnight at 100° C. and calcined at 500° C. for 2 hours (4 hours heating ramp).

The sample is then washed in 100 ml of a 2% $K_2CO_3$ solution for 1 hour (rolling board). Afterwards the sample is washed two times with 200 ml water (one hour each, rolling board). The sample is filtered and dried overnight at 100° C.

EXAMPLE 2

13.9 g $Cu(NO_3)_2.2.5H_2O$ is dissolved in 37.5 g water. The solution is used to impregnate 50 g of support (pv=1 ml/g). The sample is rolled for 1 hour, dried overnight at 100° C. and calcined at 500° C. for 2 hours (4 hours heating ramp).

The impregnation step is repeated one more time followed by drying and calcination.

The sample is then washed in 100 ml of a 2% $K_2CO_3$ solution for 1 hour (rolling board). Afterwards the sample is washed two times with 200 ml water (one hour each, rolling board). The sample is filtered and dried overnight at 100° C.

EXAMPLE 3

24 g $Fe(NO_3)_3.9H_2O$ is dissolved in 37.5 g water. The solution is used to impregnate 50 g of support (pv=1 ml/g). The sample is rolled for 1 hour, dried overnight at 100° C. and calcined at 500° C. for 2 hours (4 hours heating ramp).

The sample is then washed in 100 ml of a 2% $K_2CO_3$ solution for 1 hour (rolling board). Afterwards the sample is washed two times with 200 ml water (one hour each, rolling board). The sample is filtered and dried overnight at 100° C.

EXAMPLE 4

24 g $Fe(NO_3)_3.9H_2O$ is dissolved in 37.5 g water. The solution is used to impregnate 50 g of support (pv=1 ml/g). The sample is rolled for 1 hour, dried overnight at 100° C. and calcined at 500° C. for 2 hours (4 hours heating ramp).

The impregnation step is repeated one more time followed by drying and calcination.

The sample is then washed in 100 ml of a 2% $K_2CO_3$ solution for 1 hour (rolling board). Afterwards the sample is washed two times with 200 ml water (one hour each, rolling board). The sample is filtered and dried overnight at 100° C.

EXAMPLE 5

24 g $Fe(NO_3)_3.9H_2O$ and 0.34 g $KNO3$ are dissolved in 37.5 g water. The solution is used to impregnate 50 g of support (pv=1 ml/g). The sample is rolled for 1 hour, dried overnight at 100° C. and calcined at 500° C. for 2 hours (4 hours heating ramp).

The impregnation step is repeated one more time followed by drying and calcination.

EXAMPLE 6

16.5 g $FeSO_4.7H_2O$ and 0.9 g $KHSO_4$ are dissolved in 37.5 g water. The solution is used to impregnate 50 g of support (pv=1 ml/g). The sample is rolled for 1 hour, dried overnight at 100° C. and calcined at 500° C. for 2 hours (4 hours heating ramp).

The impregnation step is repeated one more time followed by drying and calcination.

EXAMPLE 7

17.3 g $Ni(NO_3)_2.6H_2O$ is dissolved in 37.5 g water. The solution is used to impregnate 50 g of support (pv=1 ml/g). The sample is rolled for 1 hour, dried overnight at 100° C. and calcined at 500° C. for 2 hours (4 hours heating ramp).

The sample is then washed in 100 ml of a 2% $K_2CO_3$ solution for 1 hour (rolling board). Afterwards the sample is washed two times with 200 ml water (one hour each, rolling board). The sample is filtered and dried overnight at 100° C.

EXAMPLE 8

17.4 g $Co(NO_3)_2.6H_2O$ is dissolved in 37.5 g water. The solution is used to impregnate 50 g of support (pv=1 ml/g).

The sample is rolled for 1 hour, dried overnight at 100° C. and calcined at 500° C. for 2 hours (4 hours heating ramp).

The sample is then washed in 100 ml of a 2% $K_2CO_3$ solution for 1 hour (rolling board). Afterwards the sample is washed two times with 200 ml water (one hour each, rolling board). The sample is filtered and dried overnight at 100° C.

EXAMPLE 9

9 g $MoO_3$ is dissolved in 37.5 g of $NH_4OH$ solution. The resulting solution is used to impregnate 50 g of support (pv=1 ml/g). The sample is rolled for 1 hour, dried overnight at 100° C. and calcined at 500° C. for 2 hours (4 hours heating ramp).

The sample is then washed in 100 ml of a 2% $KNO_3$ solution for 1 hour (rolling board). Afterwards the sample is washed two times with 200 ml water (one hour each, rolling board). The sample is filtered and dried overnight at 100° C.

EXAMPLE 10

17.5 g $H_2WO_4$ is dissolved in 37.5 g of $NH_4OH$ solution. The resulting solution is used to impregnate 50 g of support (pv=1 ml/g). The sample is rolled for 1 hour, dried overnight at 100° C. and calcined at 500° C. for 2 hours (4 hours heating ramp).

The sample is then washed in 100 ml of a 2% $K_2CO_3$ solution for 1 hour (rolling board). Afterwards the sample is washed two times with 200 ml water (one hour each, rolling board).

The sample is filtered and dried overnight at 100° C.

EXAMPLE 11

14.5 g $SnCl_2.2H_2O$ is dissolved in 37.5 g of $NH_4OH$ solution. The resulting solution is used to impregnate 50 g of support (pv=1 ml/g). The sample is rolled for 1 hour, dried overnight at 100° C. and calcined at 500° C. for 2 hours (4 hours heating ramp).

The sample is then washed in 100 ml of a 2% $K_2CO_3$ solution for 1 hour (rolling board). Afterwards the sample is washed two times with 200 ml water (one hour each, rolling board). The sample is filtered and dried overnight at 100° C.

EXAMPLE 12

18 g $Zn(NO_3)_2.6H_2O$ is dissolved in 37.5 g of a $NH_4OH$ solution. The resulting solution is used to impregnate 50 g of support (pv=1 ml/g). The sample is rolled for 1 hour, dried overnight at 100° C. and calcined at 500° C. for 2 hours (4 hours heating ramp).

The sample is then washed in 100 ml of a 2% $K_2CO_3$ solution for 1 hour (rolling board). Afterwards the sample is washed two times with 200 ml water (one hour each, rolling board). The sample is filtered and dried overnight at 100° C.

EXAMPLE 13

7.9 g $MoO_3$ is dissolved in 37.5 g $NH_4OH$ (25%). This solution is used to impregnate 50 g of support (pv=0.75 ml/g). The sample is rolled for 1 hour, dried overnight at 100° C. and calcined at 500° C. for 2 hours (4 hours heating ramp).

The sample is then impregnated with 7.7 g $Co(NO_3)_2.6H_2O$ and 0.8 g $KNO_3$ dissolved in 37.5 g water. The sample is rolled for 1 hour, dried overnight at 100° C. and calcined at 500° C. for 2 hours (4 hours heating ramp).

EXAMPLE 14

Results, Cu-Based Catalysts

These catalysts have been tested previously as reported in U.S. Pat. No. 3,275,705, according to which a temperature of between 649 and 660° C. was used. The present tests were run at a much lower temperature using a dilute mixture of 10% propane in nitrogen.

The catalyst prepared according to Example 1 was tested after being reduced and sulfided. The result for Cu was an activity of 72 Nl/h/kg cat of propylene at a temperature of 600° C. At 560° C., the activity was 35 Nl/h/kg cat corresponding to an activation energy of 1.13 eV.

The results reported in U.S. Pat. No. 3,275,705 are up to 320 Nl/h/kg cat. A considerable thermal cracking is expected at this temperature. If the results of the present testing are extrapolated to 660° C., an activity of 190 Nl/h/kg cat is obtained. However, this is not an initial activity. The test results reported in U.S. Pat. No. 3,275,705 are of a short duration and therefore reporting an initial activity and no lifetime. Besides that, the Cu load of the catalyst prepared according to Example 1 could easily be increased.

X-ray powder diffraction of the spent sample showed digenite, $Cu_{1.78}S$, with an average crystallite size of 18 nm.

EXAMPLE 15

Results, Fe-Based Catalysts

The iron catalysts made according to Example 3 start out as an oxide and are slowly reduced and activated during the first propane dehydrogenation (PDH) test. After the second test it is just regenerated and then exposed to the propane-containing gas. The $FeSO_4$ is reduced to FeS, a $CO_2$ peak is noted, and during the next 12 hours the activity increases, whereupon it slowly declines. This cycle is repeated twice.

Integration of the $CO_2$ peak around 75 hours gave 0.3 g of carbon corresponding to 6% on the catalyst, and further 3% of the converted carbon ended up on the catalyst. The activity of the catalyst after 100 hours was 265 Nl/h/kg cat of propylene. The spent catalyst showed the presence of FeS with a crystallite size of 10 nm.

The 12% iron catalyst was made from sulfates, which during the start-up were reduced to sulfides. This gave a quite stable activity of 160 Nl/h/cat of propylene.

In the low sulfur gas, the activity declined to 40 Nl/h/cat of propylene. Thermodynamics indicate that iron carbide, $Fe_3C$, would be the stable phase provided that the $H_2S$ level is below ~100 ppm. Indeed, X-ray powder diffraction indicated that iron was in the carbide phase, $Fe_3C$, with a crystallite size of 100 nm.

Sun et al. (Chem. Eng. J. 244, 145-151 (2014)) examined a sulfated iron catalyst supported on alumina at 560° C. and found an initial activity of 70 Nl/h/cat. After 6 cycles of regeneration it had declined to 50 Nl/h/cat. A study on isobutane by Wang et al. of Fe supported on silica at 560° C. gave an initial activity of 17 Nl/h/cat. The condition was quite close to equilibrium.

EXAMPLE 16

Results, Ni-Based Catalysts

The nickel catalyst prepared according to Example 7 showed a high activity and to some extent an activity dependent on the activity on the sulfur level. The final activity was 330 Nl/h/cat of propylene at 600° C. At 560° C., an activity of 140 Nl/h/cat was found. This corresponds to an activation energy of 1.3 eV. This is a remarkably high activity, found close to the melting point of NiS. The tests with gas 4 were conducted under circumstances where a phase transition in the NiS system could take place. The phase diagram shows some complexity above 800° K. Conversion of propane into hydrogen and propene will change the $H_2S/H_2$ ratio and thereby change the stability for a certain phase.

After regeneration, the spent catalyst showed a NiO phase with a crystallite size of 17 nm by X-ray powder diffraction. For Nickel, Wang et al. found an activity of 15 Nl/h/kg cat of isobutylene at 560° C.

EXAMPLE 17

Results, Co-Based Catalysts

The cobalt catalyst was made according to Example 8. It was started up in a low sulfur gas. However, after a number of phase transitions, the activity gradually increased. In the low sulfur gas, the state of Co is most like CoS, or $Co_9S_8$ should be formed. In a high sulfur concentration, $Co_3S_4$ may be formed. Cobalt sulfide has a homogeneity range. It is noted that $CoSO_4$ reacts with propane, giving $CO_2$. About 3% of the converted carbon ends up on the catalyst.

The final activity at 600° C. was 170 Nl/h/kg cat of propylene. At 560° C., the activity was 70 Nl/h/kg cat corresponding to an activation energy of 0.7 eV. The regenerated spent catalyst showed the presence of a $Co_3O_4$ with a crystallite size of 10 nm.

In connection with dehydrogenation of isobutane over a CoS catalyst, Chinese publications by Wang et al. have reported 42 and 15 Nl/h/kg cat of isobutylene, respectively. In the present experiment, sulfur was added as ammonium sulfate to the $Co/Al_2O_3$ catalyst, whereas Wang et al. also used co-feeding with $H_2S$.

EXAMPLE 18

Results, Mo-Based Catalysts

The Mo-based catalyst was made according to Example 9. During the tests, the carbide-sulfide interface was challenged. For up to 140 hours, the experiments were run with a low (~100 ppm) sulfur level. A rapidly declining activity is seen, probably due to formation of molybdenum carbide. At 150 hours, the sulfur level is increased and the sulfide phase is stabilized along with the activity. The cracking activity is above the background level for the sulfide/carbide catalyst. The maximum activity was 60 Nl/h/cat propene at 600° C.

The spent catalyst was examined using X-ray powder diffraction. No molybdenum phases were seen, although the chemical analysis showed a molybdenum content of 7.25 wt %.

EXAMPLE 19

Results, Co—Mo Based Catalysts 5 g of a catalyst prepared as described in Example 14 was tested. The test lasted for 3 weeks and included 10 regenerations and tests with temperatures from 520 to 640° C. The sulfur level was not in any case below 1000 ppm. Thus carbide formation could be excluded.

The starting activity was 260 Nl/h/cat and the final activity was 210 Nl/h/kg cat at 600° C. At other temperatures the corresponding maximum activities were 104 Nl/h/cat at 580° C., 100 Nl/h/cat at 560° C. and 42 Nl/h/cat at 520° C. This corresponds to an activation energy of 0.27 eV.

At the lower temperatures, the activity declined slower than at the high temperature. Runs of up to 64 hours were done, during which a decline in the activity from 1.31% to 0.57% $C_3H_6$ was seen.

Table 4 below indicates that a relation exists between the band gap energy and the activity, but also to some extent between the activation energy and the band gap, in particular for the lower activities. This could make sense when taking into consideration that, for high activities, other mechanisms than available electrons/holes could give rate limitations, such as simple transport limitations. Catalysts based on iron and nickel and possibly also on cobalt and copper will have sufficient activity for operation in the Oleflex process. In case of operation in the Catofin process they may be less suitable. A pre-reduction may be required in order to avoid loss of propane in the reduction of sulfate to sulfide. However, the activity for iron and nickel is quite high, so possibly less metal and thereby less sulfate may be required.

TABLE 4

Summary of results

| Compound | Activity Nl/h/kg cat | Activation energy (eV) | Band gap energy eV |
|---|---|---|---|
| $Cu_2S$ | 70 | 1.1 | 1.2-1.5 |
| CoS | 100 | 1.2 | 0.9 |
| $Co_3S_4$ | 170 | 1.3 | 1.15 |
| FeS | 260 | — | ~0 |
| NiS | 330 | 1.3 | 0.4 |
| $Ni_3S_2$ | 100 | 0.5 | ~0.4 |
| Co—Mo | 260 | 0.3 | ? |
| $MoS_2$ | 60 | ~0 | 1.3-1.4 |

The catalysts are deactivated slowly by carbon deposition and therefore need to be regenerated, just like the commercially available catalysts based on platinum or chromium oxide. The regeneration takes place by combustion in dilute air, i.e. 1% $O_2$ and 99% $N_2$, at 560-600° C.

Regeneration of Fe, Co, Ni and Cu sulfides using $N_2$ with 1% $O_2$ will lead formation of the corresponding sulfate, at least for Fe and Co, whereas Ni and Cu will most likely form oxides, which has been confirmed by X-ray powder diffraction of the spent samples. The Mo and W sulfides are converted into oxides. In this connection, a possible loss of active material as a volatile oxide ($MoO_3$) has to be taken into account. In order to conserve sulfur on the catalyst, regeneration should start at 400° C. followed by a carbon removal at 600° C.

Re-sulfidation using a mixture of $H_2$ and $H_2S$ in $N_2$ has often been carried out prior to the dehydrogenations tests. In some cases, this has been omitted, whereby initially a large formation of $CO_2$ was noted. Some sulfates, in particular $MnSO_4$, have shown a good selectivity for oxidative dehydrogenation of propane.

The regeneration takes the catalyst through two phase transition stages, from sulfide to sulfate or oxide and back again to sulfide. The phase transitions involve not only structural transformations, but also volume changes. Thus, in the case of NiS to $NiSO_4$ an expansion of 250% takes place. It is expected that sintering/dispersion of the system will reach steady state after a number of regenerations.

During dehydrogenation, some carbon is deposited on the catalyst, resulting in a slow deactivation. Dehydrogenation takes place for some hours followed by catalyst regeneration in $N_2$ containing 1% $O_2$. This is typically followed by a sulfidation or a direct return to dehydrogenation. In this case, a direct reaction between sulfate and propane takes place, resulting in a large $CO_2$ formation.

The carrier is treated with a dilute alkali compound and subsequently washed to remove acid sites. Preferably the dilute alkali compound is potassium carbonate or any other potassium compound.

In the experiments, the carrier has been dipped in a dilute potassium carbonate solution followed by a two-step wash in demineralized water, resulting in a potassium content of 0.15 wt %. Acid sites have been removed, but not necessarily all of them. The results indicate a pressure influence on the carbon formation, and they also indicate that carbon formation takes place from propylene, not propane. Furthermore, the results indicate that there is a complete carbon removal during regeneration.

The invention claimed is:

1. A regenerated catalyst for the dehydrogenation of alkanes to alkenes, said regenerated catalyst comprising a catalytically active material comprising a metallic sulfide (MeS) supported on a carrier, wherein the metallic sulfide (MeS) is a semiconductor, and wherein the catalyst has been regenerated in steps, wherein the steps for regeneration comprise oxidation in diluted air to avoid thermal runaway and to convert the sulfide into the corresponding sulfate and conversion back to the sulfide by reduction in dilute hydrogen comprising hydrogen sulfide.

2. The regenerated catalyst according to claim 1, wherein the metal of the metallic sulfide comprises Fe, Co, Ni, Cu, Mo or W or any combination of two or more metals selected from Pb, Sn, Zn, Fe, Co, Ni, Cu, Mo and W.

3. The regenerated catalyst according to claim 1, wherein the oxidation in dilute air is carried out at a temperature between 350 and 750° C.

4. The regenerated catalyst according to claim 1, wherein the carrier is treated with a dilute alkali compound and subsequently washed to remove acid sites.

5. The regenerated catalyst according to claim 4, wherein the dilute alkali compound is potassium carbonate or any other potassium compound.

6. A process for the dehydrogenation of alkanes to the corresponding unsaturated alkenes and hydrogen ($H_2$) comprising contacting a feed gas comprising an alkane with a regenerated catalyst according to claim 1, said catalyst being a metallic sulfide supported on a carrier and comprising Fe, Co, Ni, Cu, Mo or W or a combination of two or more metals selected from Pb, Sn, Zn, Fe, Co, Ni, Cu, Mo and W, wherein the feed gas contains sulfur in an amount determined such that
(a) the equilibrium reaction $MeS+H_2 \leftrightarrow Me+H_2S$ is shifted towards MeS throughout the reactor, and
(b) the sulfur content is sufficient to avoid carbide formation throughout the reactor.

7. The process according to claim 6, wherein the dehydrogenation is carried out at a temperature between 450 and 650° C.

8. The process according to claim 6, wherein the dehydrogenation is carried out at a pressure from 0.9 bar below ambient pressure to 5 bar above ambient pressure.

9. The process according to claim 8, wherein the dehydrogenation is carried out at ambient pressure or at a pressure from 0.5 bar below ambient pressure up to ambient pressure.

10. The process according to claim 6, wherein the $H_2S/H_2$ ratio being from $10^{-3}$ to $10^{-1}$.

11. A process for the dehydrogenation of alkanes to the corresponding unsaturated alkenes and hydrogen ($H_2$) comprising contacting a feed gas comprising an alkane with a catalyst for the dehydrogenation of alkanes to alkenes, said catalyst comprising a catalytically active material supported on a carrier, wherein the catalytically active material comprises a metallic sulfide (MeS), wherein the metallic sulfide (MeS) is a semiconductor, said catalyst being a metallic sulfide supported on a carrier and comprising Fe, Co, Ni, Cu, Mo or W or a combination of two or more metals selected from Pb, Sn, Zn, Fe, Co, Ni, Cu, Mo and W, wherein the feed gas contains sulfur in an amount determined such that
(a) the equilibrium reaction $MeS+H_2 \leftrightarrow Me+H_2S$ is shifted towards MeS throughout the reactor, and
(b) the sulfur content is sufficient to avoid carbide formation throughout the reactor.

12. The process according to claim 11, wherein the $H_2S/H_2$ ratio being from $10^{-3}$ to $10^{-1}$.

* * * * *